March 5, 1968 J. H. ASPER Plant Pat. 2,798
CAMELLIA PLANT
Filed Sept. 8, 1966
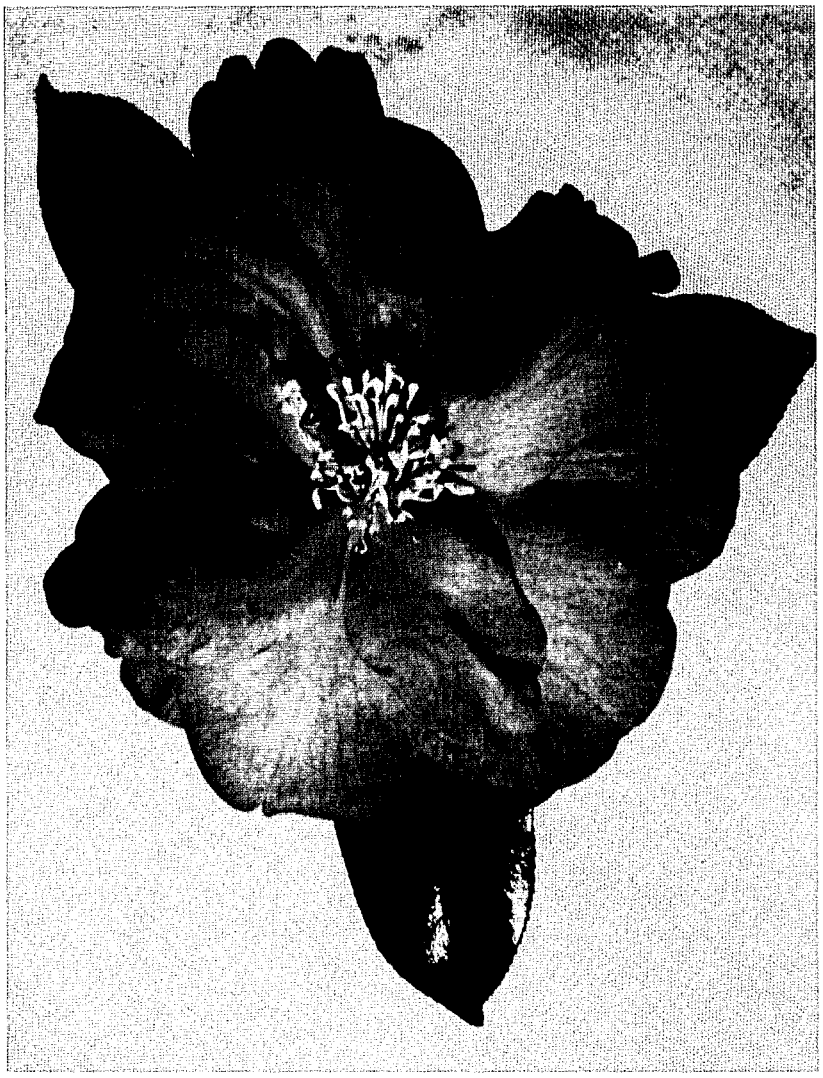
INVENTOR.
J. HOWARD ASPER
BY J. F. Cunes
ATTORNEY United States Patent Office Plant Pat. 2,798
Patented Mar. 5, 1968

2,798
CAMELLIA PLANT

James Howard Asper, Escondido, Calif., assignor to Select Camellias, Inc., Whittier, Calif., a corporation of California Filed Sept. 8, 1966, Ser. No. 578,106
1 Claim. (Cl. Plt.—62)

The present invention relates to a new and distinct variety of camellia plant of the semi-double type.

The new and distinct variety is characterized by its large semi-double type blooms that vary in color from Blood Red shading to a Cardinal Red. The blooms exhibit a pronounced fluorescence. The plant exhibits a vigorous, upright spreading growth habit and has large, very dark green, heavy and thick waxy leaves with substantially serrated margins.

The new variety was produced by me on my property located in Escondido, Calif. by cross breeding *Camellia japonica* "Donckelari," an unpatented variety, as the seed parent, and *Camellia reticulata* "Lion Head," also an unpatented variety, as the pollen parent. This cross breeding was performed in 1958, and when the plant first bloomed in 1960, it bore the large, dark red, fluorescent blooms that had substantially black stamens when these were mature.

The new variety is distinguished from its seed parent, *Camellia japonica* "Donckelari," in that this parent has variegated flowers whereas the flowers of the new variety are a deep fluorescent red. The new variety is distinguished from its pollen parent in that the pollen parent also bears variegated flowers of a red and white combination.

Asexual reproduction of my new variety is accomplished by cuttings and graftings. The numerous cuttings made by me in Escondido, Calif., all showed the foregoing characteristics and these same characteristics were transmitted through succeeding propagations, thereby establishing that the strain is true. The plant will not reproduce true from seed.

The accompanying illustration in full color, shows a flower of the new variety and includes some of the leaves. This colored illustration is as correct as it is possible to reproduce the fluorescent red of the flowers by this form of illustration.

A detailed description of my new variety follows: to facilitate the identification of the important colors referred to in this specification, the color terminology adopted by the British Horticultural Colour Charts has been adopted.

*The plant*

Parentage:
- *Seed parent.*—*Camellia japonica* Donckelari.
- *Pollen parent.*—*Camellia reticulata* Lion Head.
- Both parent plants are unpatented varieties.

Form: Bush.

Growth habit: Vigorous, spreading and upright.

Foliage:
- *Quantity.*—Abundant.
- *Size.*—Leaves are up to three and three-quarter inches in length and range up to two inches in width at the widest portion.
- *Shape.*—The leaves are broadly elliptic with the apex of the leaf being acuminate. The base of the leaves is obtuse.
- *Texture.*—Heavy, thick and waxy.
- *Color.*—Upper side—the upper side of the leaves is approximately Ivy Green ooo1060/2. Under side—the under side of the leaves is Spinach Green o960/1.
- *Ribs and veins.*—The veins and ribs are ordinary, and are not too prominent.
- *Leaf margins.*—Serrulate to serrate.

Petiole: Petioles are short, these being about three-eighths of an inch in length.

Leaf arrangement: The leaves are alternate on the stem and are more widely spaced than usual. Ordinarily the leaves are about three-quarter of an inch apart while in the present variety, the leaves are one and one-half inches apart on an average.

Wood: New wood has a bright green color that exhibits a slight fluorescence. Old wood is greyish-brown in color.

*The flower*

Blooming habit: This variety is a so-called mid-season bloomer with the normal flowering period commencing the early part of February and extending usually to the end of March and sometimes into April; the flowering period is given for the coastal region of southern California.

Buds:
- *Size.*—Large.
- *Form.*—Oval shaped and pointed.
- *Sepals.*—Smooth edged.

Bloom (when fully open):
- *Size.*—Classed as very large being usually five inches in diameter.
- *Borne.*—Usually more than one on a stem. The stems are relatively short for so large a flower.
- *Form.*—Semi-double type flower.
- *Petalage.*—Imbricated.
- *Color.*—The color of the flowers is Cardinal Red 8 22/1 with some portion of the petals shading to Blood Red 8 20 to 8 20/1. A definite fluorescence can be seen.
- *Petals.*—Shape—usually orbicular with apex retuse. Texture—petals are very thick and have a waxy texture. There are usually 21 petals.

Genital organs:
- *Stamens.* — Type — dorsifixed. Number — approximately ninety one arranged in a circle. Color—when the flower is in its early stages of opening stamens are Barium Yellow 503/3 as the flower remains fully opened for a considerable time these stamens assume a brownish hue and when fully mature the stamens are almost black.
- *Filaments.*—Color—the filaments of a flower that has completely opened are Claret Rose o21/2. Length—filaments are about ¾" in length.
- *Pollen.*—Color—yellow when ripe.

I claim:

1. A new and distinct variety of camellia plant substantially as herein shown and described, characterized particularly as to novelty by its large semi-double type blooms that are predominantly Blood Red in color shading to Cardinal Red and having a pronounced fluorescence, by its orbiculate petals with the apex retuse, by its substantially black stamens when these are mature, by its large, very dark green leaves that are heavy, thick and waxy and have serrated margins, and by its vigorous, upright spreading growth habit.

No references cited.

ROBERT E. BAGWILL, *Primary Examiner.*